(12) United States Patent
Jin et al.

(10) Patent No.: US 8,932,633 B2
(45) Date of Patent: Jan. 13, 2015

(54) POLYSACCHARIDE MICROPARTICLES CONTAINING BIOLOGICAL AGENTS: THEIR PREPARATION AND APPLICATIONS

(75) Inventors: Tuo Jin, Highland Park, NJ (US); Fei Wu, Shanghai (CN); Weien Yuan, Shanghai (CN)

(73) Assignee: Biopharm Solutions Inc., Highland Park, NJ (US)

( * ) Notice: Subject to any disclaimer, the term of this patent is extended or adjusted under 35 U.S.C. 154(b) by 823 days.

(21) Appl. No.: 12/065,310

(22) PCT Filed: Jul. 20, 2006

(86) PCT No.: PCT/CN2006/001777
§ 371 (c)(1),
(2), (4) Date: Feb. 29, 2008

(87) PCT Pub. No.: WO2007/025441
PCT Pub. Date: Mar. 8, 2007

(65) Prior Publication Data
US 2008/0248098 A1 Oct. 9, 2008

Related U.S. Application Data

(60) Provisional application No. 60/712,548, filed on Aug. 29, 2005.

(51) Int. Cl.
| | |
|---|---|
| A61K 9/16 | (2006.01) |
| A61L 31/12 | (2006.01) |
| A61L 31/10 | (2006.01) |
| A61L 27/48 | (2006.01) |
| A61K 9/00 | (2006.01) |
| A61K 9/70 | (2006.01) |
| A61K 39/00 | (2006.01) |
| A61K 9/19 | (2006.01) |

(52) U.S. Cl.
CPC ............ *A61K 9/1694* (2013.01); *A61K 9/1623* (2013.01); *A61K 9/0024* (2013.01); *A61L 31/129* (2013.01); *A61K 9/7007* (2013.01); *A61L 31/10* (2013.01); *A61K 9/1647* (2013.01); *A61L 27/48* (2013.01); *A61K 39/00* (2013.01); *A61K 9/19* (2013.01); *A61K 9/1652* (2013.01)
USPC ................... 424/489; 424/130.1; 424/184.1; 424/488; 424/499

(58) Field of Classification Search
None
See application file for complete search history.

(56) References Cited

U.S. PATENT DOCUMENTS

| | | | |
|---|---|---|---|
| 4,891,319 A * | 1/1990 | Roser | ............................ 435/188 |
| 5,417,982 A | 5/1995 | Modi | |
| 5,716,644 A | 2/1998 | Zale et al. | |
| 5,827,707 A | 10/1998 | Lamberti | |
| 6,303,148 B1 | 10/2001 | Hennink et al. | |
| 6,805,879 B2 | 10/2004 | Jin et al. | |
| 6,998,393 B2 * | 2/2006 | Jin et al. | .......................... 514/57 |
| 2002/0055461 A1 | 5/2002 | Jin | |
| 2003/0059402 A1 * | 3/2003 | Jin et al. | ....................... 424/93.2 |
| 2004/0234616 A1 | 11/2004 | Sabetsky | |

FOREIGN PATENT DOCUMENTS

| | | |
|---|---|---|
| CN | 1054009 A | 8/1991 |
| JP | 2004510724 T | 4/2004 |
| WO | WO 96/40071 | 12/1996 |
| WO | WO 98/00170 | 1/1998 |
| WO | WO 98/22093 A1 | 5/1998 |
| WO | WO 00/41682 A | 7/2000 |
| WO | WO 02/00778 | 1/2002 |
| WO | WO 03/101600 A2 | 12/2003 |
| WO | WO 03101600 A2 * | 12/2003 |

OTHER PUBLICATIONS

H-Q Mao, K Roy, VL Troung-Le, KA Janes, KY Lin, Y Wang, JT August, KW Leong. "Chitosan-DNA nanoparticles as gene carriers: synthesis, characterization and transfection efficiency." Journal of Controlled Release 70 (2001) 399-421.*

(Continued)

*Primary Examiner* — Frederick Krass
*Assistant Examiner* — Isaac Shomer
(74) *Attorney, Agent, or Firm* — Law Offices of Albert Wai-Kit Chan, PLLC

(57) ABSTRACT

A method of preparing polysaccharide glassy microparticles which are less than 10 μm in diameter and contain structurally delicate agents, such as proteins, peptides, gene materials, vaccines, antibodies, viruses and liposomes using low-temperature aqueous-aqueous emulsification (free of polyelectrolytes) and freezing-induced phase separation. When delicate agents are added to a polysaccharide-PEG two phase system followed by homogenization (or other shear adding process), the agents partition into the polysaccharide dispersed phase preferentially. These processes help to avoid aggregation of proteins caused by interaction with charged polyelectrolytes used for stabilizing the polysaccharide dispersed phase in our previously reported aqueous-aqueous emulsion. When this system is frozen and lyophilized, glassy particles less than 10 μm in diameter containing delicate agents can be formed. These fine polysaccharide particles protect proteins within their hydrophilic glassy matrix, and can therefore be easily suspended in hydrophobic polymer solutions and formulated to various forms of sustained release devices such microsphere, sheets, fibers, coating layers, and scaffolds. The particles can also be dispersed in hydrophilic gels to improve releasing kinetics and to deliver vaccines and antibodies for immune therapy.

6 Claims, 15 Drawing Sheets

(56) References Cited

OTHER PUBLICATIONS

BC Heng, H Yu, SC Ng. "Strategies for the Cryopreservation of Microencapsulated Cells." Biotechnology and Bioengineering, vol. 85 Issue 2, Nov. 25, 2003, pp. 202-213.*
MC Heller, JF Carpenter, TW Randolph. "Manipulation of Lyophilization-Induced Phase Separation: Implications for Pharmaceutical Proteins." Biotechnology Progress, vol. 13, 1997, pp. 590-596.*
Written Opinion, Nov. 16, 2006, for Jin et al., International Application No. PCT/CN2006/001777, Filed Jul. 20, 2006.
International Search Report, Nov. 16, 2006, for Jin et al., International Application No. PCT/CN2006/001777, Filed Jul. 20, 2006.
International Search Report, Aug. 28, 2003, for Biopharm Solutions Inc., International Application No. PCT/CN03/000431, Filed Jun. 3, 2003.
Canadian Office Action, Nov. 18, 2010, for Biopharm Solutions Inc., Canadian Application No. 2,487,867, Filed Nov. 29, 2004, National Stage of PCT/CN03/000431, Filed Jun. 3, 2003.
European Office Action, Aug. 19, 2010, for Biopharm Solutions Inc., European Application No. 03737838.7, filed Dec. 17, 2004, National Stage of PCT/CN03/000431, Filed Jun. 3, 2003.
Extended European Search Report, Nov. 9, 2010, for Biopharm Solutions Inc., European Application No. 06761512, filed Feb. 29, 2008, National Stage of PCT/CN06/017777, Filed Jul. 20, 2006.
Japanese Office Action, Jan. 5, 2010, for Biopharm Solutions Inc., Japanese Application No. 2004-508943, filed Nov. 24, 2004, National Stage of PCT/CN03/000431, Filed Jun. 3, 2003.
Taiwanese Office Action, Nov. 10, 2004, for Biopharm Solutions Inc., Taiwanese Application No. 91,136,977, filed Dec. 23, 2002.
Taiwanese Office Action, Mar. 9, 2006, for Biopharm Solutions Inc., Taiwanese Application No. 91,136,977, filed Dec. 23, 2002.
US Office Action, May 20, 2003, for Biopharm Solutions Inc., U.S. Appl. No. 10/291,327, filed Nov. 8, 2002.
US Office Action, Nov. 4, 2003, for Biopharm Solutions Inc., U.S. Appl. No. 10/291,327, filed Nov. 8, 2002.
US Office Action, Mar. 3, 2004, for Biopharm Solutions Inc., U.S. Appl. No. 10/291,327, filed Nov. 8, 2002.
US Office Action, Sep. 24, 2004, for Biopharm Solutions Inc., U.S. Appl. No. 10/291,327, filed Nov. 8, 2002.
US Office Action, Jul. 27, 2007, for Biopharm Solutions Inc., U.S. Appl. No. 10/517,122, flied Dec. 2, 2004, National Stage of PCT/CN03/000431, Filed Jun. 3, 2003.
Bartus et al., 1998, "Sustained delivery of proteins for novel therapeutic products", Science, 281:1161-1162.
Berthold et al., 1996, "Preparation and Characterization of Chitosan Microspheres as Drug Carrier for Prednisolone Sodium Phosphate as Model for Antiflammatory Drugs", Journal of Controlled Release, 39.17-25.
Bittner et al., 1998, "Recombinant Human erythropoietin(rhEPO) loaded poly(lactide-co-glycolide) microspheres: Influence of the encapsulation technique and polymer purity on microsphere characteristics", Eur. J. Pharm. Biopharm, 45:295-305.
Burke, P.A., 2000, "Controlled release protein therapeutics: effects of process and formulation on stability", Handbook of pharmaceutical controlled release technology, Marcel Dekker, 661-692.
CAS, 2002, Results of search on chemical abstracts on the subject of sustained release of proteins based on degradable polymers.
Cleland, J.L. and Jones, L.S., 1996, "Stable formulations of recombinant human growth hormone and interferon- for microencapulation in biodegradable microspheres", Pharm Res, 13:1464-1475.
Cunningham et al., 1991, "Dimerization of human growth hormone by zinc", Science, 253:545-546.
Franssen, O and Hennick, W.E., 1998, "A novel preparation method for polymeric microparticles without the use of organic solvents", Intern. J. Pharm, 168:1-7.
Goodman and Gilman, 1996, "The Pharmacological Basis of Therapeutics", 10th Ed., 54-57.
Johnson, O.L., 1987, "The stabilization and encapsulation of human growth hormone into biodegradable microspheres", Pharmaceutical Research, 14:730-735.
Langer, R, Folkman, J., 1976, "Polymers for the sustained release of proteins and other macromolecules", Nature, 263:797-800.
Liu et al., 1991, "Moisture-induced aggregation of lypholized proteins in the solid state", Biotech. Bioeng., 37:177-184.
Maa et al., 1998, "Spray-drying of air-liquid interface sensitive recombinant human growth hormone", J. Pharm. Sci., 87:152-159.
Morita et al., 2000, "Formation and osolation of spherical fine protein microparticles through lypholization of protein-poly(ethylene glycol) aqueous mixture", Pharm Res, 17:1367-1373.
Morita et al., 2001, "Preparation of gelatin microparticles by co-lyophilization with poly(ethylene glycol): characterization and application to entrapment into biodegradable microspheres", International Journal of Pharmaceutics, 219:127-137.
Morlock et al., 1997, "Microencapsulation of rh-erythropoietin, using biodegradable poly (D,L-lactide-co-glycolide):protein stability and the effects of stabilizing excipients", European Journal of Pharmaceutics and Biopharmaceutics, 43:29-36.
Park et al., 1998, "A new preparation method for protein loaded poly(D,L-lactic-co-glycolic acid) microspheres and protein release mechanism study", J Controlled Release 55:181-191.
Maria Jose Blanco Prieto et al., 1994, "Characterization of V3 BRU peptide-loaded small PLGA microspheres prepared by a (w1/o)w2 emulsion solvent evaporation method", International Journal of Pharmaceutics, 111 (2):137-145.
Sanchez, A et al., 1999, "Formulation strategies for the stabilization of tetanus toxoid in poly(lactide-oo-glycolide) microspheres", Intern. J. Pharm., 185;255-266.
Schwendeman et al., 1996, Stability of proteins and their delivery from biodegradable polymer microspheres S.C.M. Bernstein, Ed., Microparticulate Systems for the Deiivery of Proteins and Vacines, Mercel Decker, NY vol. 77:1-49.
Schwendeman et al., 1998, "New strategies for the microencapsulation of tetanus vaccine", J Microencapsulation, 15:299-318.
Takahata et al., 1998, "The Distribution of protein associated with poly(DL-lactide co-glycolide) microparticles and its degradation in simulated body fluids", J Controlled Release, 50.237-248.
Yoshioka et al., 1997, "Dependence of the molecular mobility and protein stability of freeze-dried-globulin formulations on the molecular weight of dextran", Pharmaceutical Research, 14:736-741.
Weert et al., 2000, "Protein instability in poly(lactic-co-glycolic acid) mictroparticles", Pharm. Res., 17:1159-1167.
Weert et al., 2000, "Lysozyme distribution and conformation in a biodegradable polymer matrix as determined by FTIR techniques", J Controlled Release, 68:31-40.

* cited by examiner

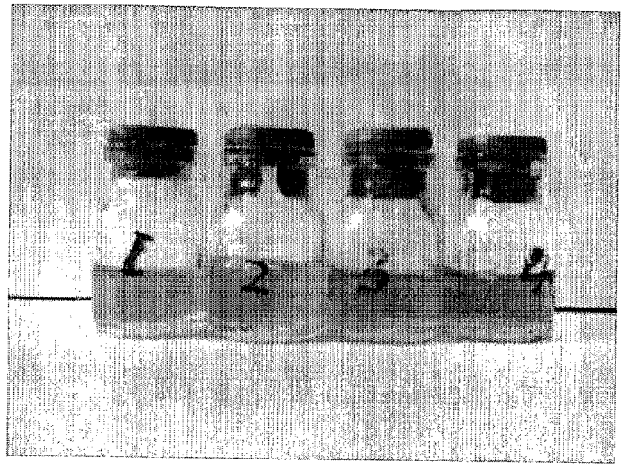
(A). Photo image of an aqueous-aqueous emulsion prepared below 4C;
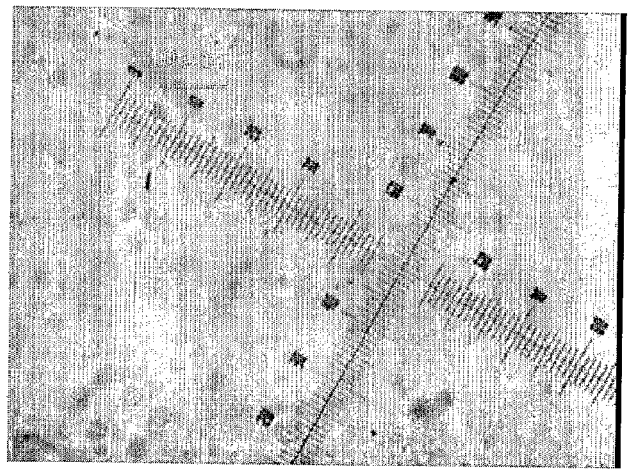
(B). Microscopic image of the aqueous-aqueous emulsion of (2).
Figure 1. Myoglobin-loaded Low temperature aqueous-aqueous emulsion

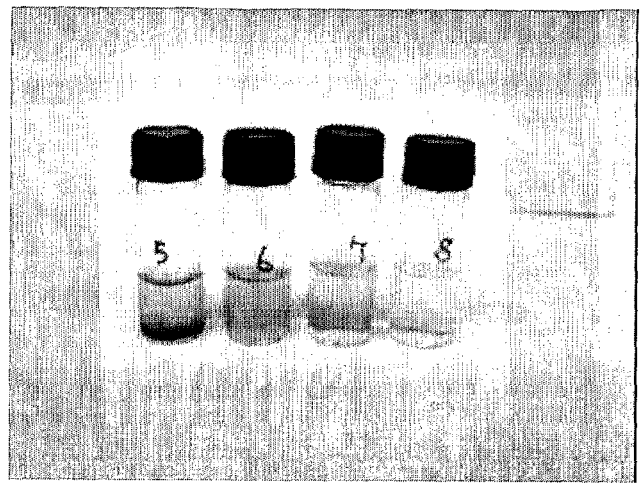
Figure 2. Myoglobin-loaded uniform aqueous polymers solution
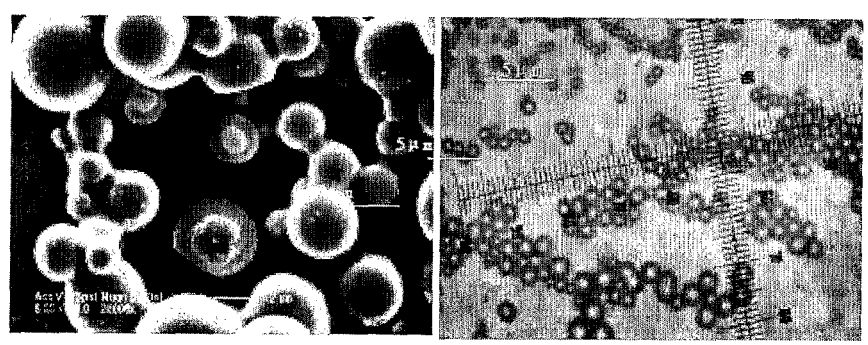
Figure 3A. SEM and Light Microscopic Pictures of polysaccharide glassy particles for the method 1

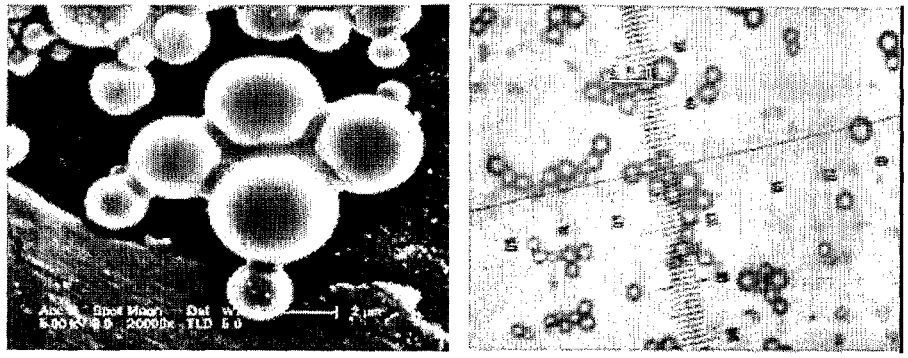
Figure 3B. SEM and Light Microscopic Pictures of polysaccharide glassy particles for the method 2
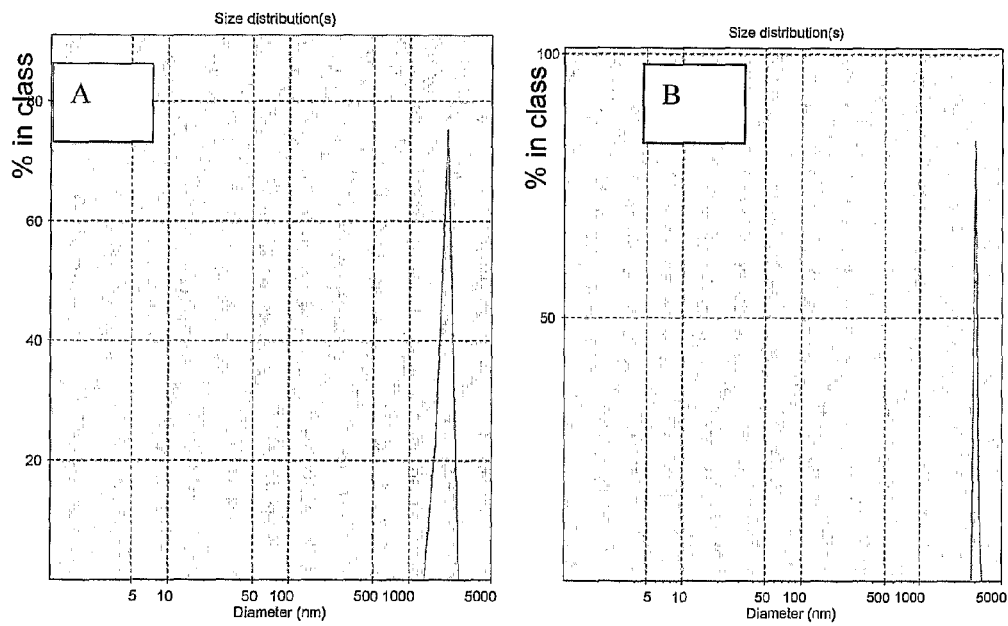
Fig.4. Size distribution of 3 formed using freezing induced phase separation and low temperature aqueous-aqueodu emulsification.
A: freezing induced phase separation;
B: low temperature aqueous-aqueodu emulsification.

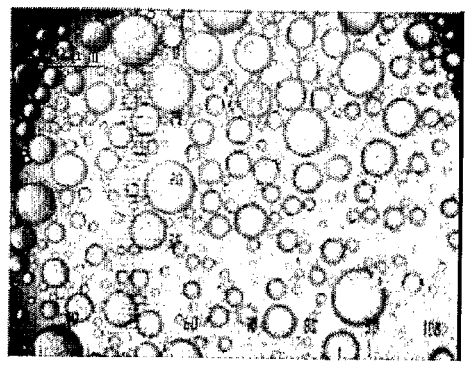

A: Light microscopic images of PLGA microspheres containing AqueSpheres before hardening;

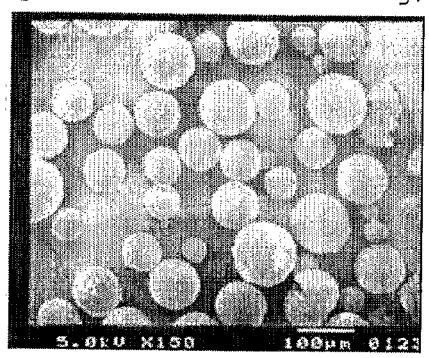

B: Electromicroscopic images of PLGA microspheres containing AuqeSpheres after hardening.

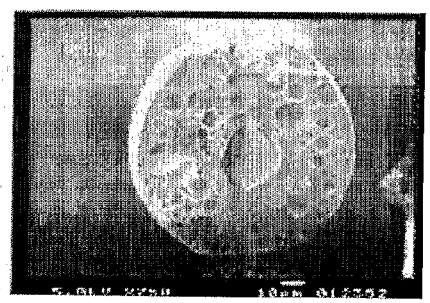

C: Electromicroscopic images of freeze-fractured PLGA microspheres containing AqueSpheres after hardening.

Fig. 5. Microscopic images of PLGA microspheres containing AqueSpheres.

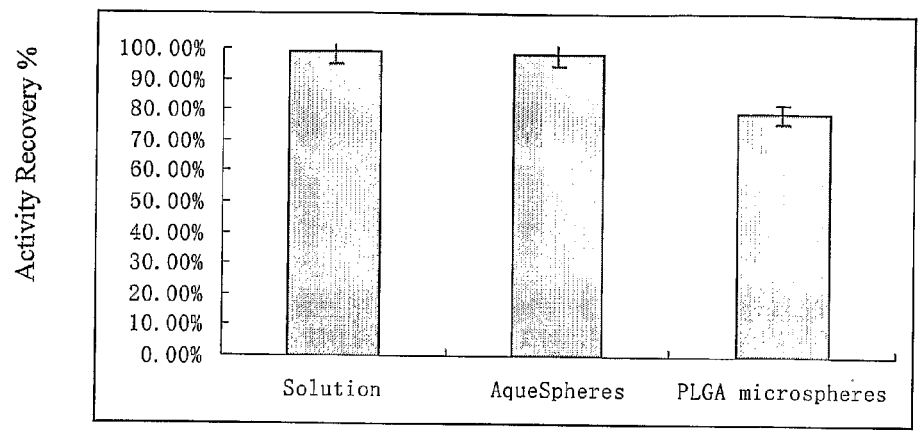
A: freezing induced phase separation (FIPS);
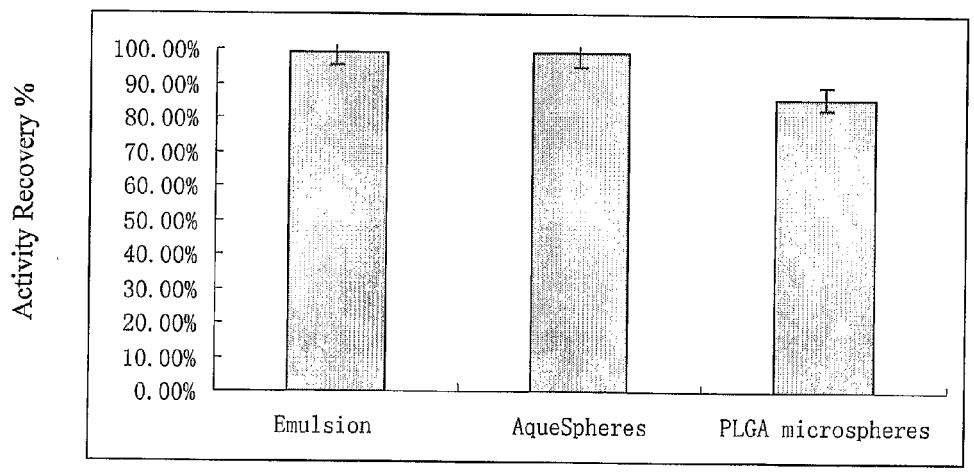
B: low temperature aqueous-aqueodu emulsification (LTAAE).
Fig. 6. Catalytic activity of β-galactosidase in o-nitrophenyl-b-D-galactopyrannoside (ONPG) oxidation recovered from each step of preparing process of PLGA microspheres using AqueSpheres.

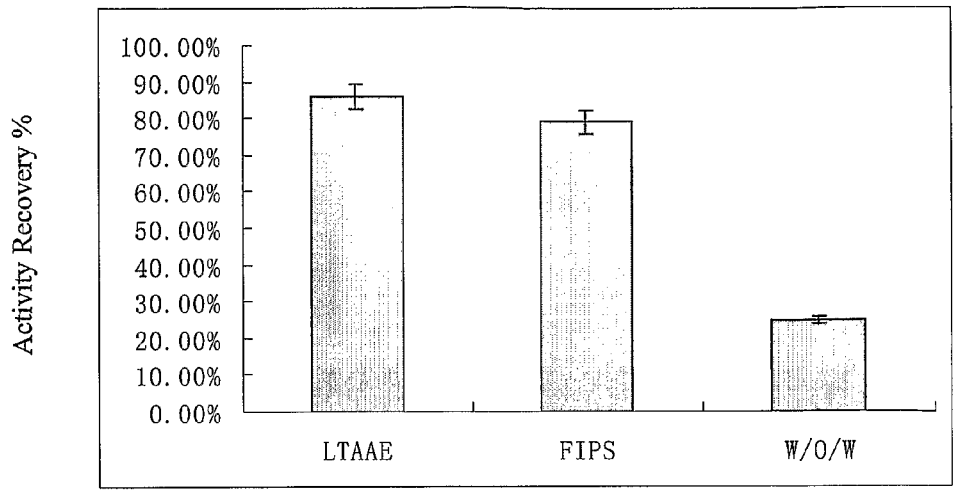
Fig. 7. Comparison of Catalytic activity of recovered β-galactosidase in o-nitrophenyl-b-D-galactopyrannoside (ONPG) oxidation between various preparation methods.
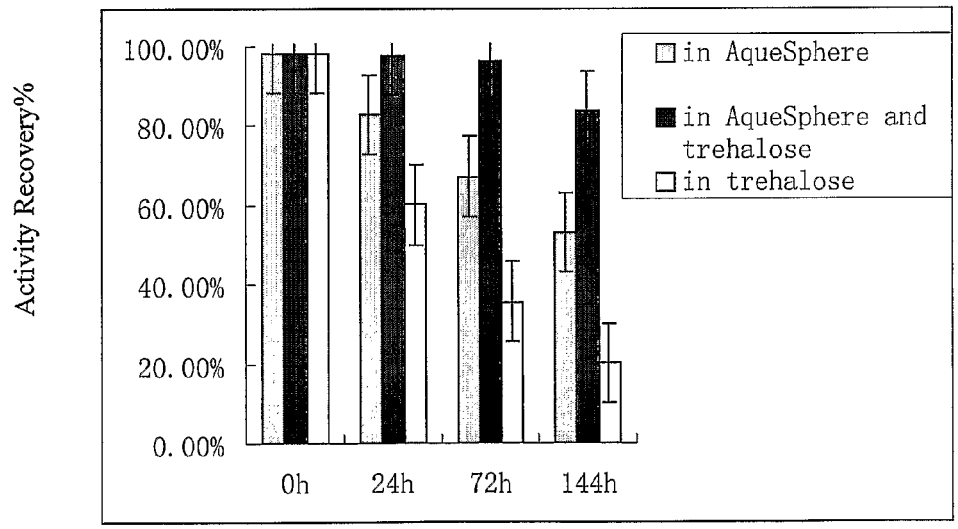
Fig. 8. Catalytic activity of β-galactosidase formulated in various methods and incubated at 37 °C for prolonged time.

(1)
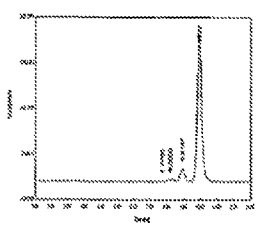 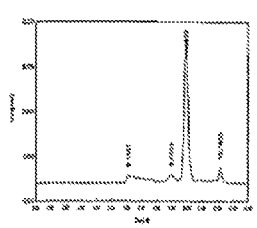 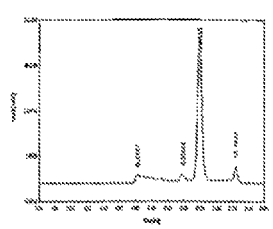
Standard Myglobin: 89.6860%monomers   Myglobin-dextran: 89.0260%monomer   Mylgobin PLGA: 88.7660%monomers
(2)
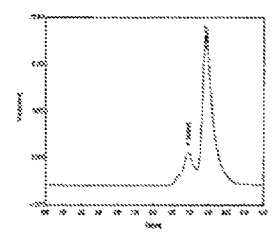 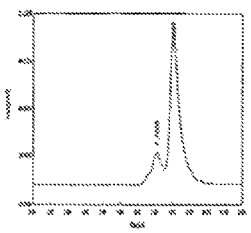 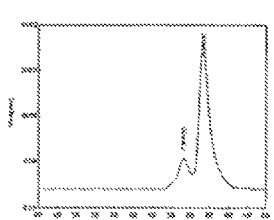
Standard BSA: 82.2436%monomers   BSA-dextran: 82.5684%monomer   BSA-PLGA: 82.2133%monomers
Fig. 9A (1)
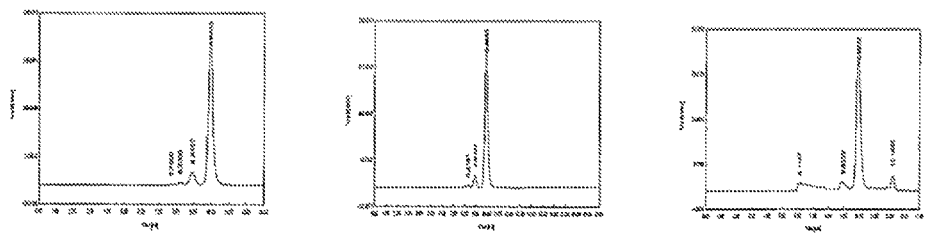
(2)
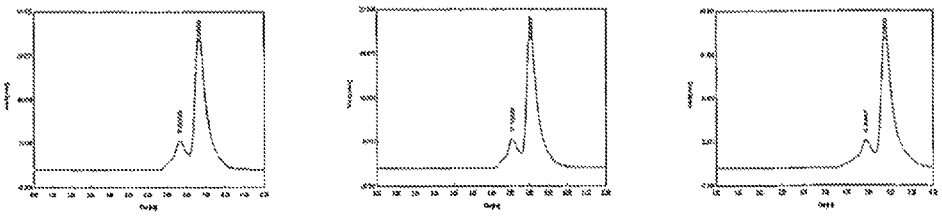
Fig. 9B

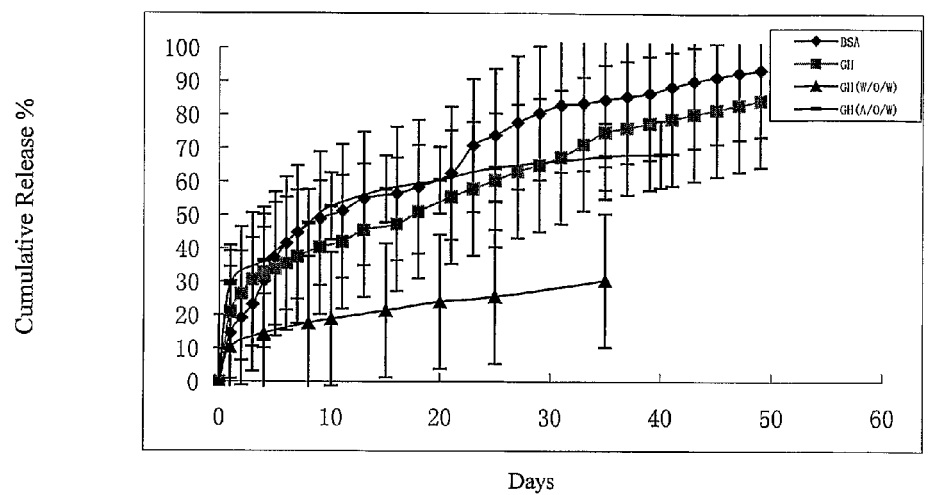
Fig. 10. Release profiles of BSA and rhGH from microspheres prepared of PLGA 50/50 in L/G ratio and 30KD in $\langle M_w \rangle$ using the method of this invention.

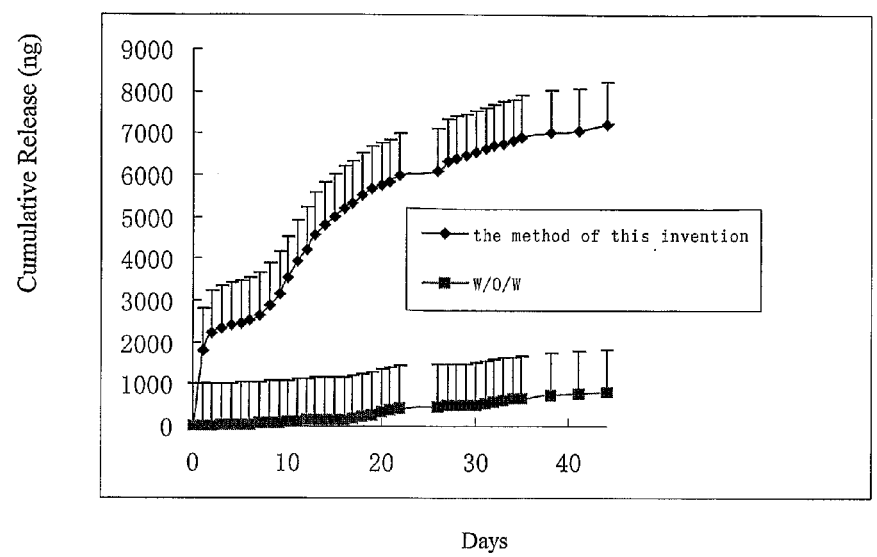
Fig. 11. Release profile β-galactosidase from PLGA (50/50 in L/G ratio and 12KD in $<M_w>$) microspheres prepared using the present invent and conventional W-O-W methods.

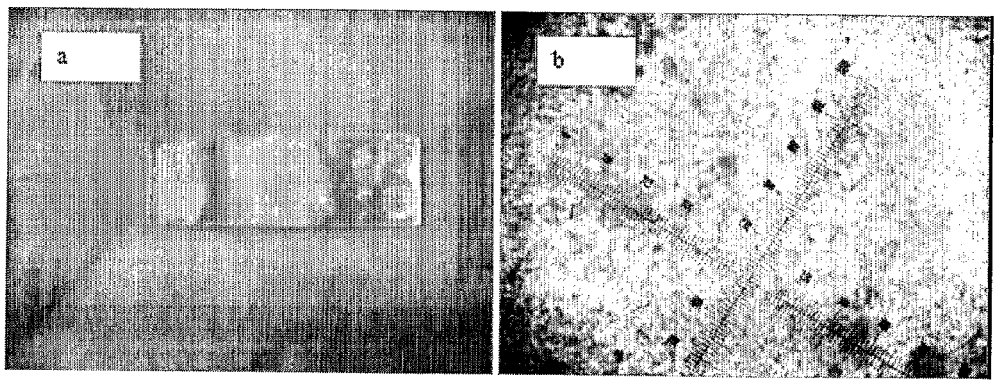

A. The microscopic images of protein-containing AqueSpheres dispersed in a PLGA sheet
a: photo of sheet;b: Light Microscopic Pictures of a(1000x)

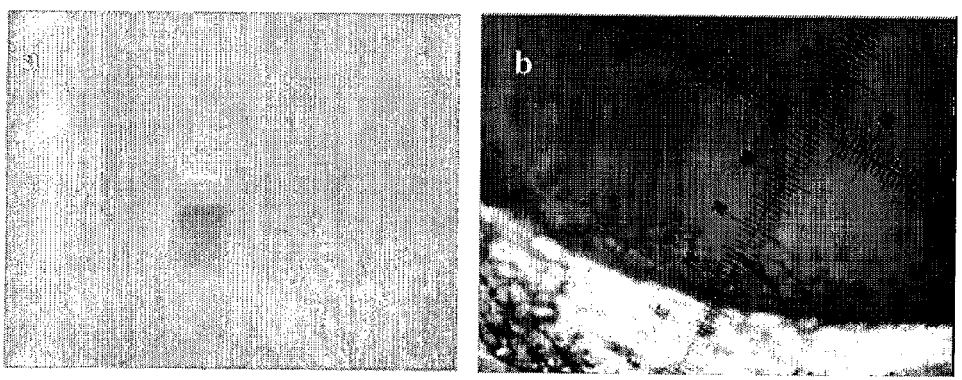

a: photo of sheet;b: Light Microscopic Pictures of a(1000x)
B The microscopic images of protein-containing AqueSpheres dispersed in a PLGA scaffold.

Figure 12A and 12B microscopic images of protein-containing AqueSpheres dispersed in a PLGA sheet and a PLGA scaffold.

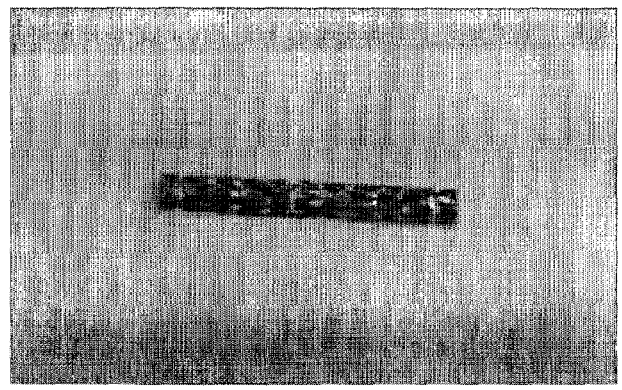
Figure 13 Photograph of a stent coated with a layer of PLGA in which myoglobin-containing AqueSpheres are dispersed.
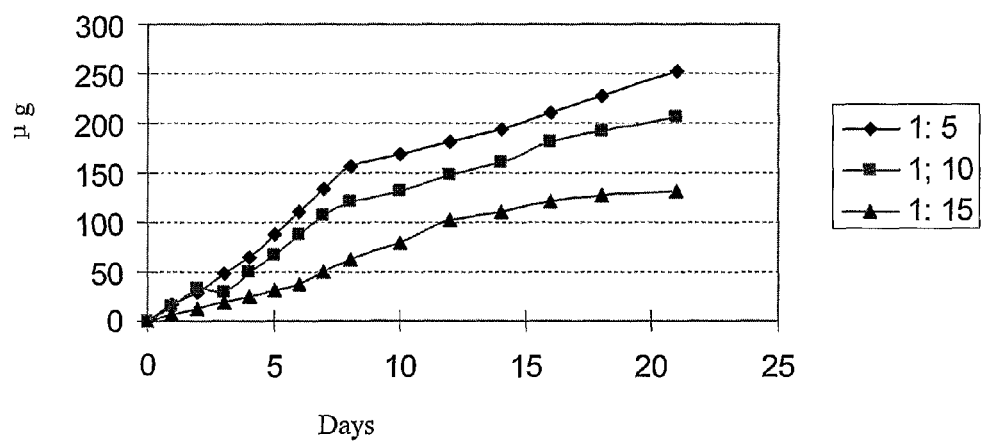
Figure 14 Release profiles of myoglobin from the PLGA coating on stents, for which the protein release rate varies as a function of polysaccharide content.

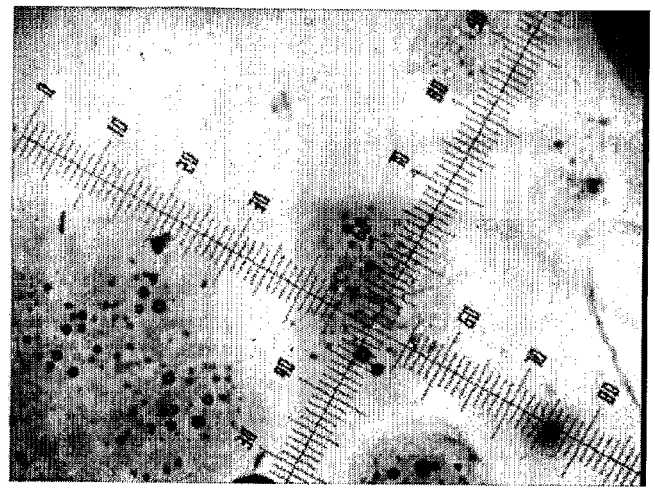
Figure 15 shows the microscopic images of AqueSpheres dispersed in the PLGA-PEG-PLGA thermal sensitive gels.

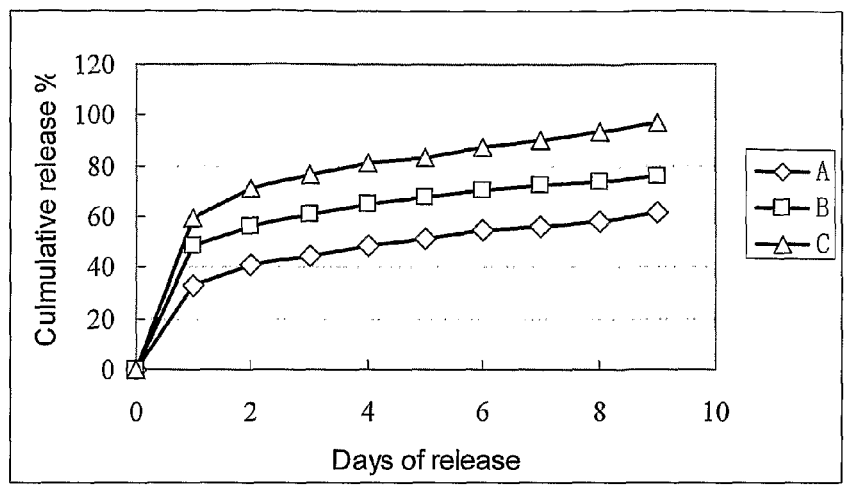
Figure 16. Release profiles of BSA loaded as AqueSperes or as free molecules into thermal sensitive gels.
A) BSA was preloaded in AqueSpheres prepared using stable aqueous-aqueous emulsification; B) BSA was preloaded in AqueSpheres prepared using freezing induced phase separation; C) BSA was directly added to the thermal sensitive gel.

A: the electro-microscopic images for nanometer-sized AqueSpheres containing a model subunit vaccine (for hepatitis E)

B: PLGA microspheres containing nanometer-sized AqueSpheres

Figure 17 Electro-microscopic images for nanometer-sized AqueSpheres containing a model subunit vaccine (for hepatitis E) and PLGA microspheres containing such AqueSpheres.

POLYSACCHARIDE MICROPARTICLES CONTAINING BIOLOGICAL AGENTS: THEIR PREPARATION AND APPLICATIONS

CROSS REFERENCES AND RELATED APPLICATIONS

This application is the National Stage of International Application NO. PCT/CN2006/001777, filed Jul. 20, 2006 which claims priority of U.S. provisional Application No. 60/712,548, filed Aug. 29, 2005, the entire disclosure of which is incorporated by reference herein in its entirety.

BACKGROUND OF THE INVENTION

When structurally delicate agents, such as proteins, peptides, gene materials, viruses, vaccines, antibodies or liposomes are loaded in degradable polymer-based drug delivery systems, the contact with organic solvents (which are required to dissolve the polymers) often causes denaturation of these agents [1-3]. To avoid this denaturation, proteins and peptides were prepared into solid particles with sugars or polysaccharides prior to encapsulation into water-insoluble polymer devices [4-7]. For sustained-release purposes, the protein-containing sugar or polysaccharide particles should be small enough (<10 μm) to avoid severe burst in the initial stages of release [4, 5]. Pre-loading proteins or peptides into small particles of aqueous polymers prior to encapsulation by degradable polymer devices may also improve release kinetics of the loaded devices by minimizing burst and incomplete release [5, 8].

Loading proteins into fine polysaccharide particles can be a formidable task due to the fact that reported particle-forming methods generally involve the use of organic solvents, interfacial tension (such as water-oil interfaces or water-air interfaces and other hydrophilic/hydrophobic interfaces), shear stress, elevated temperatures, and other conditions that are hazardous to the loaded proteins. However, there have been some progresses in the field.

We (Jin, et al.) disclosed a unique system, aqueous-aqueous emulsion, for loading delicate proteins into polysaccharide fine particles under conditions without organic solvents, strong interface tension, strong shear stress, and elevated temperatures [5, 8]. Proteins can be loaded into the dispersed polysaccharide phase thermodynamically by preferential partition under such mild conditions.

This system, however, is compromised with some drawbacks. For example, it requires relatively concentrated aqueous solutions of two hydrophilic polymers (a polysaccharide and a PEG solution) and usage of a third water-soluble polymer, a polyelectrolyte with a negative charge on its backbone, to form an aqueous-aqueous emulsion and to stabilize the dispersed polysaccharide phase from fusion [5, 8]. If solubility of the protein is low, the ratio of polysaccharide/protein will be too high so that loading capacity for proteins will be too low (since the concentration of polysaccharide must be high enough for phase separation). In addition, some proteins may interact strongly with the polyelectrolyte, which is required for forming a stable aqueous-aqueous emulsion, to form ionically complexed aggregates.

Consequently, there is much demand for a method of encapsulating structurally delicate proteins and/or peptides into a matrix of degradable polymer-based drug delivery systems, where the proteins and/or peptides will not be denatured in the process and will be released in a controlled manner. Pre-loading proteins into polysaccharide fine glassy particles is an effective way to preserve protein activity during the formulation process due to its resistance to organic solvents [5]. The present invention offers some improvements over previously reported methods [5,8] by avoiding charged polyelectrolytes, such as sodium alginate. The present invention also extends the usage of fine polysaccharide glassy particles for sustained-release of proteins from microspheres to various polymer-based devices, implants or injectable therapeutics.

SUMMARY OF THE INVENTION

The present invention discloses two methods for the preparation of fine polysaccharide glassy particles containing one or more structurally delicate agents, such as proteins, peptides, gene materials, vaccines, antibodies, viruses or liposomes without the use of polyelectrolytes, such as sodium alginate.

For method 1, one or more of the agents, such as proteins, one or more polysaccharides, and polyethylene glycol (PEG) are dissolved in water above the critical concentration for phase separation (i.e., having a concentration in single phase region). The immiscible solutions are stirred or homogenized at a temperature close to their freezing points (at least below 10° C.), followed by freezing, lyophoilizing, and rinsing with organic solvents as above. The result of the above process is fine polysaccharide glassy particles encapsulating the proteins.

For method 2, one or more of the agents, such as proteins, one or more polysaccharides, and polyethylene glycol (PEG) are dissolved in water below the critical concentration for phase separation (i.e., having a concentration in single phase region). The solution is then slowly frozen, followed by lyophilization. Afterwards, the PEG is removed by rinsing the lyophilized powder with an organic solvent (such as methylene chloride, acetonitrile, or acetone). This process results in similar polysaccharide glassy particles as method 1.

These glassy particles can be microencapsulated in degradable polymer microspheres or loaded into other degradable polymer devices (such as scaffolds, films, fibers, sheets, coatings of drug-eluting stents, or thermal sensitive gels) for sustained-release of the agents loaded in the glassy phase. Due to the resistance of the polysaccharide glassy particles to organic solutions, structurally delicate agents such as proteins can be well protected from denaturation during various formulation processes.

The methods of this invention can also be used to prepare nanometer sized glassy particles for vaccination and antibody therapy. Antigenic proteins may be loaded in sustained-release polymer microspheres through glassy particles and released in nature conformation and a sustained profile for prolonged antibody titer.

For treatment of tumors using antibodies, the antibody can be loaded using this invention in sustained-release polymer microspheres that can be injected in the region of a solid tumor for localized and prolonged antibody action. For targeting to certain organs which are not feasible for site-specific injection (such as liver), the antibody-carrying microspheres can be made in a size which facilitate up-take by reticular endothelial system of the organ.

DETAILED DESCRIPTION OF FIGURES

FIG. 1. Low temperature aqueous-aqueous emulsion.

(A). Photo image of low-temperature aqueous-aqueous emulsion prepared below 4° C.;

(1) after mixing 0.50 ml 10 w/w % dextran (containing 0.4 w/w % myoglobin) with 2.5 ml 10 w/w % PEG;

(2) after mixing 0.28 ml 10 w/w % dextran (containing 0.72 w/w % myoglobin) with 2.8 ml 10 w/w % PEG;

(3) after mixing 0.15 ml 10 w/w % dextran (containing 1.34 w/w % myoglobin) with 3.0 ml 10 w/w % PEG;

(4) after mixing 0.1 ml 10 w/w % dextran (containing 2.0 w/w % myoglobin) with 3.0 ml 10 w/w % PEG.

(B). Microscopic image of the aqueous-aqueous emulsion of (2).

FIG. 2. Solutions containing dextran, PEG, myoglobin.

(5) after mixing 0.25 ml 10 w/w % dextran (containing 0.8 w/w % myoglobin) with 2.5 ml 10 w/w % PEG;

(6) after mixing 0.25 ml 10 w/w % dextran (containing 0.4 w/w % myoglobin) with 2.5 ml 5 w/w % PEG;

(7) after mixing 0.25 ml 2.5 w/w % dextran (containing 0.2 w/w % myoglobin) with 2.5 ml 2.5 w/w % PEG;

(8) after mixing 0.25 ml 1.25 w/w % dextran (containing 0.1 w/w % myoglobin) with 2.5 ml 1.25 w/w % PEG.

FIG. 3. Microscopic images of polysaccharide glassy particles prepared using the methods of this invention (called AuqeSpheres hereafter).

A: SEM (left) and Light (right) microscopic images of AuqeSpheres formed by freezing induced phase separation;

B: SEM (left) and Light (right) microscopic images of AqueSpheres formed by low temperature aqueous-aqueous emulsification.

FIG. 4. Size distribution of 3 formed using freezing induced phase separation and low temperature aqueous-aqueous emulsification.

A: freezing induced phase separation;

B: low temperature aqueous-aqueous emulsification.

FIG. 5. Microscopic images of PLGA microspheres containing AqueSpheres.

A: Light microscopic images of PLGA microspheres containing AqueSpheres before hardening;

B: Electromicroscopic images of PLGA microspheres containing AuqeSpheres after hardening.

C: Electromicroscopic images of freeze-fractured PLGA microspheres containing AqueSpheres after hardening.

FIG. 6. Catalytic activity of β-galactosidase in o-nitrophenyl-b-D-galactopyrannoside (ONPG) oxidation recovered from each step of preparing process of PLGA microspheres using AqueSpheres. 1% trehalose was added in preparation of AqueSpheres for both methods.

A: freezing induced phase separation (FIPS);

B: low temperature aqueous-aqueous emulsification (LTAAE).

FIG. 7. Comparison of Catalytic activity of recovered β-galactosidase in o-nitrophenyl-b-D-galactopyrannoside (ONPG) oxidation between various preparation methods.

FIG. 8. Catalytic activity of β-galactosidase formulated in various methods and incubated at 37° C. for prolonged time. Comparison was made between the protein in hydrated AqueSpheres containing 1% trehalose, that in hydrated AqueSpheres not containing trehalose, and that in 10% trehalose solution.

FIG. 9A. SEC-HPLC charts for myoglobin (1) and BSA (2) recovered from AuqeSpheres and PLGA microspheres prepared through freezing induced phase separation, before and after various treatments.

FIG. 9B. SEC-HPLC charts for myoglobin (1) and BSA (2) recovered from AqueSpheres and PLGA microspheres prepared through low temperature aqueous-aqueous emulsification, before and after various treatments.

FIG. 10. Release profiles of BSA and rhGH from microspheres prepared of PLGA 50/50 in L/G ratio and 30 KD in $<M_w>$ using the method of this invention. The release buffer and the protein concentration assay were the same as in FIG. 10.

FIG. 11. Release profile β-galactosidase from PLGA (50/50 in L/G ratio and 12 KD in $<M_w>$) microspheres prepared using the present invent and conventional W-O-W methods. The protein released was assayed by its catalytic activity in ONPG oxidation.

FIG. 12 Microscopic images of protein-containing AqueSpheres dispersed in a PLGA sheet (A) and a PLGA scaffold (B).

FIG. 13 Photograph of a stent coated with a layer of PLGA in which myoglobin-containing AqueSpheres are dispersed.

FIG. 14 Release profiles of myoglobin from the PLGA coating on stents, for which the protein release rate varies as a function of polysaccharide, content.

FIG. 15 Microscopic images of AqueSpheres dispersed in the PLGA-PEG-PLGA thermal sensitive gels before and after its gellation.

FIG. 16 Release profiles of BSA loaded as AqueSperes or as free molecules into thermal sensitive gels.

A) BSA was preloaded in AqueSpheres prepared using stable aqueous-aqueous emulsification; B) BSA was preloaded in AqueSpheres prepared using freezing induced phase separation; C) BSA was directly added to the thermal sensitive gel.

FIG. 17 Electro-microscopic images for nanometer-sized AqueSpheres containing a model subunit vaccine (for hepatitis E) and PLGA microspheres containing such AqueSpheres.

DETAILED DESCRIPTION OF THE INVENTION

The present methods for preparing polysaccharide particles containing structurally delicate agents, such as proteins, peptides, vaccines, gene materials, antibodies, viruses or liposomes, is based on an aqueous two-phase separation, the same chemical principle also used in our previously-reported stable aqueous-aqueous emulsion system [5,8]. An aqueous two-phase state provides a particle-forming mechanism free of organic solvents and hydrophilic/hydrophobic interfacial tension, major factors causing protein denaturing during the formulation process. In our previously disclosed method involving the stable aqueous-aqueous emulsion system [5], a relatively concentrated polysaccharide solution and a polyelectrolyte, such as sodium alginate, are needed to form separated aqueous two phases and to stabilize the dispersed phase by forming a diffuse double layer around the droplets, respectively. However, the required high concentration of polysaccharide limit the loading capacity of proteins of low solubility, and the use of a polyelectrolyte may cause aggregation of some proteins. Accordingly, and unlike previously disclosed methods, the present method provides an alternative way to prepare polysaccharide particles containing structurally delicate agents, such as proteins, without the use of a polyelectrolyte.

Without a polyelectrolyte, and thus the diffuse double layer around the dispersed phase that is generated by the charged polymer, the dispersed droplets fuse and form two block phases immediately after removing the shear stress (such as stirring). A self-standing aqueous-aqueous emulsion cannot persist. Thus, to avoid formation of block phases, methods that stabilize aqueous droplets in an aqueous continuous phase without using polyelectrolytes are used in the present invention. The two methods to stabilize the dispersed aqueous droplets from aggregation and fusion are both based on low temperature processes: low-temperature aqueous emulsification and freezing-induced aqueous two-phase separation.

For the method 1, fusion of the polysaccharide dispersed phase is prohibited by the viscosity increase of the system at low temperature. When the two aqueous polymer solutions are mixed at a temperature close to freezing point (at least lower than 10° C.), the polysaccharide dispersed phase has no time to fuse in a viscous continuous phase prior to freezing. Polysaccharide glassy particles may easily be formed by lyophilization of the frozen aqueous polymer emulsions.

The method 2 is due to the fact that aqueous two-phase separation is a function of concentration and temperature of the two hydrophilic polymers solutions [10]. At a given temperature, the two aqueous polymer solutions form separated phases when their concentrations are above a critical point. Below the critical concentration, the two polymer solutions are miscible and form a clear, one-phase solution. The critical concentration, however, is a function of temperature. As temperature drops down, the critical concentration (for phase separation) is lowered. The phase diagram shifts when the temperature is dropped below the critical temperature so that phase separation is resulted. Since the system temperature is close to the freezing point and the mobility of the dispersed phase is substantially low and is frozen before fusion occurs. Another possible mechanism may be that free ice forms in the system during temperature dropping so that the concentration of the polymers increases over the critical point for phase separation. Since this phase separation occurs during the process of continuous ice forming (freezing point temperature), the dispersed phase has no chance to fuse to form a block phase, but remains as fine particles. For whatever the mechanisms, dispersed polysaccharide phase can be formed and frozen, and can be converted to solid particles by lyophilization.

Morita, et al. demonstrated a process by co-dissolving a protein into a PEG solution [7]. With a PEG to protein ratio larger than 1, the protein formed particles during freezing. After lyophilization, followed by removing PEG with dichloromethane, solid protein microparticles were obtained. Our previous experiment [8] showed, however, for sustained release from a degradable polymer depot, the protein should be protected in a polysaccharide matrix to reduce protein aggregation and the interaction the hydrophobic polymer. In the present invention, modified aqueous two-phase separation techniques are used to prepare polysaccharide glassy particles for microencapsulation of biological agents, such as proteins, peptides, gene materials, vaccine, viruses, antibodies or liposomes.

Compared with a PEG-protein system, a PEG-polysaccharide system is easier to achieve aqueous two-phase separation [7, 10]. If a water soluble protein exists in the PEG-polysaccharide system, the protein will partition between the PEG and polysaccharide phases during the phase separation [11]. For most of soluble proteins and other soluble biological agents, especially glycoproteins, this partition normally favors the polysaccharide phase. Liposomes are partitioning in the polysaccharide phase preferentially too.

Based on the above discussion, structurally delicate agents (such as proteins) can easily be packed into fine polysaccharide glassy particles. Delicate proteins possess tertiary and/or quaternary structure, and these higher conformations are easily changed by physical environment.

For low-temperature emulsification method, proteins are first added in a polysaccharide solution and then mixed into a PEG solution (both of the polymer solutions are above the phase separation concentration), followed by freezing, lyophilization and removing the continuous phase by re-dissolving PEG.

For freezing-induced phase separation method, a co-solution containing PEG, a polysaccharide, and a protein below their critical concentrations of phase transition (between one-phase and two-phase) is prepared. The PEG/polysaccharide ratio should be set to ensure that the polysaccharide forms the dispersed phase during the freezing-induced concentration process. To ensure phase separation to occur during freezing, the clear co-solution is placed in a freezer to gradually freeze (avoid immediate freezing such as contacting with dry ice or liquid nitrogen in order to give the system a chance for phase-separation). During slow freezing, the PEG-polysaccharide phase separation occurs and protein has sufficient time to reach partition equilibrium. The frozen sample is then lyophilized, followed by removal of the PEG phase using an organic solvent, such as dichloromethane.

Porosity of the obtained polysaccharide microparticles can be estimated by re-suspending them in dichloromethane (density=1.325), chloroform (density=1.495), and carbon tetrachloride (density=1.592), respectively. A density above 1.5 indicates that the particles are solid, glassy and nonporous.

Phase separation during freezing of dextran/PEG co-solution has been previously reported as a cause for denaturation of proteins with quaternary structure [12, 13]. In these reports however, the authors did not demonstrate the usage of phase separation to prepare polysaccharide particles less than 10 μm in diameter. The dextran particles formed during this freezing-induced phase separation are 10 μm or larger in diameter [12,13].

For protein denaturation during freeze-induced phase separation, the authors attributed protein denaturing to the interfacial tension between the two separated phases formed by the freezing process. This seems not the case in the present case.

In our previous invention [8], we examined bioactivities of three proteins (GM-CSF, EPO and -galactosidase with tertiary and quaternary structure, respectively) which were mixed together with an aqueous system containing dextran and PEG. The protein containing detran-PEG two-phase system was homogenized, frozen and lyophilized, and their bioactivity was assayed using corresponding method after each step of the treatment [8]. For GM-CSF and EPO (which possess tertiary structure only), there was no significant change in their activity after each step of the treatment. For β-galactosidase, a protein with quaternary structure, its activity in ONPG oxidation dropped significantly only after the later step, lyophilization, but remained unchanged after homogenization and freezing (See reference [8] and Example 5). Since large interface area between dextran and PEG existed during homogenization and freezing, it is unlikely that the protein denaturing was resulted from interface tension between the dextran phase and the PEG phase. In addition, dextran-PEG two-phase system is well used for protein partition and purification for decades [11].

To elucidate the mechanistic details of protein denaturing during lyophilization with the dextran-PEG two-phase system, we add traholose (a lyophilization protector) in such system, and found that the protein activity was well preserved even after lyophilization (See reference [8] and Example 5). We therefore conclude that under our experiment conditions, dehydration of the lyophilization removed water molecules surrounding proteins so that the protein surface is exposed to air, leading proteins to denature. Small molecular sugars, such as trehalose, are more flexible than polysaccharides so that may provide a hydrophilic environment surrounding proteins during dehydration.

The fine glassy polysaccharide particles (<10 μm in diameter) of the present invention (for both method 1 and method 2) are not swollen by hydrophobic organic solvents, thus affording the encapsulated proteins with strong resistance to the solvents. The particles made by this method can be small enough (<10 μm in diameter, and better <5 μm) to be suspended uniformly in polymer solutions.

These properties of polysaccharide particles demonstrated in the present invention are useful for loading structurally delicate agents into various polymer-based drug delivery systems, implants and medical devices with their bioactivity preserved. The fine glassy particles can easily be suspended into an organic solution of polymer or polymers, and be formulated into the forms as microspheres, sheets, fibers, coatings of protein drug eluting stents and scaffolds.

The polysaccharide-phase (of the fine particles) protects delicate agents from the hydrophobic environment of the matrix of degradable polymers, and helps them to gradually release from the matrix in a sustained profile (like demonstrated in our previous invention [8]). Even in a hydrated state (such as after injection), the hydrated polysaccharide serves as a viscous inner phase that hydrophilic microenvironment around the loaded agents to reduce their contact with hydrophobic co-polymers [8].

The polysaccharide glassy particles prepared using the methods of this invention as well as that of our previous [5,8] can be used for local sustained-release of antibodies, a class of large, structurally complicated and delicate proteins. This nature is useful for antibody-based therapy of tumors. Tumor cells, especially those of solid tumors, release cytokines to stimulate growth of blood vessels surrounded that provide nutrients needed for wild growth of tumors [16,17]. Administration of antibodies to directly neutralize these cytokines represents an alternative immunotherapy to address various immune escape mechanisms of solid tumors [18,19]. However, large dose of antibody and nonspecific suppressing of blood vessels may be issues to concern. Site-specific administration of sustained-release dosage forms of antibodies offers a solution to inhibit the blood vessel growth in the region surrounding solid tumors only so that a prolonged antibody action may be reached by a minimized dose.

For some solid tumors for which site-specific injection may not be feasible (liver and lung tumors for example), the antibody carrying sustained-release microspheres can be prepared as few microns in diameter so that they may accumulated by the reticular-endothelial system of these organs after injection.

For delivery of subunit vaccines, the sustained-release microspheres, normally as tens of microns in diameter, can be used for prolonged antigen exposure and prolonged antibody titers [15]. The microspheres can also be prepared as small as 200-1000 nm in diameter to target antigen-presenting cells to stimulate cellular response to the antigens. In the later case, the polysaccharide glassy particles (i.e. AqueSpheres) need to be prepared as small as 50-300 nm in diameter in order to be further encapsulated in degradable polymer microspheres of the sizes above.

The polysaccharide particles may also be suspended in thermo-sensitive gels to improve sustained release profile of therapeutic agents. For example, for a so called "ReGel" system made of PLGA-PEG-PLGA block co-polymers [20], proteins loaded are distributed in the hydrophilic PEG domain, and are released rapidly after injection [21]. Although the system gels after injection into body, the permeability resistance may not be enough to sustain protein release. Moreover, the temperature induced gellation (from solution to gel) is accompanied by squeezing water out of the matrix, a process causing initial burst of water soluble loadings.

When the hydrophilic polysaccharide phase is dispersed in the PLGA-PEG-PLGA thermal sensitive gel, the particles are most likely located in its hydrophilic PEG domains between the hydrophobic PLGA matrixes. The polysaccharide phase remains immiscible with the PEG phase due to the phase-separation effect discussed above. When the thermal sensitive system gels at higher temperature, these highly hydrophilic droplets (hydrated polysaccharide particles) retain water and proteins, and resist to the volume shrinking of the gel, so that burst release of proteins loaded in polysaccharide phase of the gel is moderated. This mechanistic hypothesis is supported by our preliminary result is shown in Example 10.

EXAMPLES

The present invention provides, as the first time, an alternative way to our previous invention [5,8] to prepared fine polysaccharide glassy particles (AqueSpheres) without using organic solvent, water-air interfaces and surface active agents. With this method, delicate agents can be formulated into AqueSpheres without contact with organic solvents, strong surface tension, strong shear stress, and other chemicals that may be hazardous to the agents to be loaded. Structurally delicate agents (proteins, peptides, gene materials, viruses, and liposomes) loaded in AqueSpheres are protected by the polysaccharide matrix during various formulation processes and in vivo applications as those prepared using polyelectrolytes. This invention also extends applications AqueSpheres to fabrication of various sustained-release devices and formulations for delicate agents in addition to microspheres such as sheets, fibers, scaffolds, surface coatings, and gels.

The invention will be better understood by reference to the Examples which follow, but those skilled in the art will readily appreciate that the specific examples are only illustrative and are not meant to limit the invention as described herein, which is defined by the claims which follow thereafter.

Example 1

Preparation of Polysaccharide Glassy Particles (AqueSpheres) Using Low Temperature Aqueous-Aqueous Emulsification A fairly stable aqueous-aqueous emulsion was prepared by simply mixing a 10 w/w % dextran solution (containing 2 w/w % myoglobin) with a 10 w/w % PEG solution at 0-4° C. A small molecular sugar, trehalose (1 w/w %) was added in the dextran solution as protein stabilizer for lyophilization. FIG. 1 shows photo and microscopic images of the aqueous-aqueous stored in a refrigerator for 1 hour. The sample was removed from the refrigerator and images were quickly taken before the dispersed phase fuses at elevated temperature.

The size of the dispersed dextran phase (the droplets) ranged between 3-7 μm in diameter, similar to those prepared using polyelectrolyte stabilizers at room temperature [5,8]. This emulsion sample was then frozen at −20° C., followed by lyophilization and dichloromethane-washing to remove the continuous PEG phase. Photo and microscopic images of the obtained particles (AqueSpheres) were shown in FIG. 3A, similar to those prepared by freezing-induced dextran/PEG phase separation (FIG. 3B). The size reduction from 3-7 to 1-3 μm by lyophilization is due to dehydration.

Example 2

Preparation of Polysaccharide Glassy Particles (AqueSpheres) Using Freezing-Induced Phase Separation For a solution system containing dextran and PEG, its phase separation is a function of temperature, and concentration and molecular weight of the hydrophilic polymers [11]. In order to prepare a solution which is single phase at room temperature but becomes two phases (dispersed and continuous phases), a series of solutions containing dextran, PEG and myoglobin but different in concentrations were prepared at room temperature. A small molecular sugar, trehalose (1 w/w %) was added in the dextran solution as protein stabilizer for lyophilization. FIG. 2 shows photographs of the mixed solutions of various concentrations of dextran, PEG and myoglobin (See the figure legend for FIG. 1). Among these samples, that formed by mixing two solutions each containing 10 w/w % dextran and 10 w/w % PEG separated to two phases. All the other samples with lower concentration of dextran and PEG remained as one phase, indicating that 5 w/w % for dextran and PEG is below the critical concentration of phase separation at room temperature. We therefore used 5 w/w % dextran and PEG solutions to prepare AqueSpheres. FIG. 3B shows the electronic and optical microscopic images of the product obtained after lyophilization and removing the PEG continuous phase (by washing with dichloromethane). The particles are uniform in size (ranged 1-3 um in diameter), with a density between 1.4 and 1.59 (as examined by suspending in chloroform and carbon tetrachloride).

The size of AqueSpheres prepared using both of the methods were also assayed using a {Mastersizer} nano-particle sizer. The result (FIG. 4) is consistent with that from microscopic observation (FIG. 3), the sample prepared using freezing-induced phase separation seems slightly more uniform than the other (comparison between FIG. 4A and FIG. 4B).

Example 3

Encapsulation of AqueSpheres into PLGA Microspheres

Protein containing fine polysaccharide glassy particles (AqueSpheres) may easily encapsulated in PLGA microspheres using a solid-in-oil-in-water (S-O-W) method used in our previous invention [8]. In brief, AqueSphares were suspended in a dichloromethane solution of PLGA, then the suspension was added into a containing polyvinyl alcohol 0.5-1.5 w/w %) and NaCl (5-10 w/w %) at 1/6 volume ratio under stirring. Once a composite double emulsion was formed, this S-O-W system was immediately added large cold water (~0-10° C.) under gentle stirring for preliminary hardening, followed by aging and rinsing (to remove polyvinyl alcohol and NaCl). The PLGA microspheres obtained were lyophilized again to remove water and solvent residues prior to storage.

FIG. 5A shows the optical microscopic images of the PLGA droplets before (left) and after (right) preliminary hardening. FIGS. 5B and 5C show electroscopic images of the hardened PLGA microspheres and their freeze-fracture. The PLGA microspheres ranged 50-100 μm in diameter (FIG. 5B) with AqueSpheres dispersed in the polymer matrix (FIG. 5C).

Example 4

Activity Assay of β-galactosidase After Each Microcapsulation Step

To examine the effectiveness of the present invention in protein microencapsulation, β-galactosidase, an enzyme possessing quaternary structure and 500 KD in molecular weight, was added in dextran solutions (containing 1% trehalose) followed by the microencapsulation steps mentioned above. The protein was reconstituted after each step and assayed for bioactivity in oxidation of ONPG. FIG. 5 shows the result of activity assay. Compared with aqueous-aqueous emulsification, hyophilization and washing with dichloromethane did not cause significant change in the catalytic activity of β-galactosidase for both methods of AqueSphere preparation (FIG. 6), indicating that the protein was well protected by the polysaccharide matrix during lyophilization and dichloromethane-washing. When the protein-containing AqueSpheres were encapsulated in and recovered from PLGA microspheres, the protein activity dropped to 80% for the sample made by freezing induced phase separation, and 85% for the sample by low temperature aqueous-aqueous emulsion (FIG. 6). The lost in activity after recovery from PLGA microspheres may be due to lowered recovery yield of the protein that cannot be avoided for small amount operation. The difference between the two methods (freezing-induced phase separation and low temperature aqueous-aqueous emulsification) is within experiment error.

The protein activity recovery from PLGA microspheres prepared according to this invention is compared with that prepared using that of conventional water-in-oil-in-water (W-O-W) method in FIG. 7. Activity recovered of the proteins from microspheres made by conventional W-O-W method is only 25%, 3-4 times lower than that by the present methods, indicating protein protection effect of AqueSpheres in microencapsulation process.

Example 5

Activity Change of β-galactosidase During Incubation in Hydrated State at 37° C.

To simulate how the polysaccharide phase dispersed in PLGA matrix protect proteins loaded in it, AqueSpheres containing β-galactosidase (and trehalose as described in Examples 1 and 2) were hydrated by water twice of the polysaccharide in mass and incubated at 37° C. for days. As controls, the same protein was incubated in 10% trehalose solution at the same temperature. For the proteins loaded in hydrated AqueSpheres, the catalytic activity slightly declined versus time, and over 80% of activity remained after 6 days incubation (FIG. 8). In the case of that dissolved in trehalose solution, however, the protein activity cropped to less than 20% of original during the same period of time (FIG. 8). The polysaccharide phase can, even at hydrated state, protect delicate proteins effectively.

Example 6

SEC-HPLC Analysis on Protein Aggregation

Aggregation of therapeutic proteins during formulation process of sustained-release dosage forms often cause many undesired consequences such as loss of therapeutic activity, incomplete release and immunogenecity. In this invention, protein aggregation after various steps of microencapsulation was examined using SEC-HPLC. FIGS. 9A and 9B show the SEC-HPLC results of myoglobin and BSA recovered from polysaccharide glassy particles (AqueSpheres, prepared using two methods of this invention) and PLGA microspheres, respectively. For neither of the samples, the fraction of protein dimers was significantly higher than that of the original, indicating that no protein aggregation resulted from the microencapsulation process of the present invention (FIGS. 9A-9B).

Example 7

Sustained-Release Profiles of Various Proteins from PLGA Microspheres Prepared Using Present Invention Burst and incomplete release are a common technical challenge in formulating polymer-based sustained-release dosage forms. For proteins, the issue becomes more complicated for that the release kinetics has to compromise with the usage of various conformation stabilizers of these macromolecules. For example, small molecular sugars and salts used for protein stabilizing often generate high osmotic pressure inside of polymer microspheres, and also are released readily after hydration due to their high solubility in water. We hypothesize that using polysaccharide stabilizers which are less soluble and diffusive may improve the release profiles.

To examine how AqueSpheres may effect release kinetics, myoglobin, BSA, rhGH and β-galactosidase were loaded into AqueSpheres (according to method 1 and 2 of the present invention) then microencapsulated in PLGA microspheres through a S-O-W process.

FIG. 10 shows the release profiles of BSA and rhGH from microspheres prepared of PLGA 50/50 in L/G ratio and 40 KD in $<M_w>$ using the method of this invention. As a control, rhGH was also loaded into PLGA microspheres using conventional W-O-W method. Both proteins microencapsulated using the present invention showed a sustained-release profile with burst (for the first day) and incomplete (for over 40 days) release less than 20%. For the sample prepared using conventional W-O-W method, only 25% of the loadings were release over the same time (FIG. 10).

Similar result was obtained for a larger protein, β-galactosidase (FIG. 11). While the proteins microencapsulated in PLGA microspheres through AqueSpheres showed a sustained release profile, that microencapsulated using conventional W-O-W method showed a severe incomplete release over the same time period (FIG. 11). For β-galactosidase, since the protein quantity was below the detracting limit by micro-BCA, the assay was based its catalytic activity in ONPG oxidation, thus the release curves only reflect the protein remained to be active after experienced formulation process and release incubation.

Example 8

Loading AqueSpheres Into PLGA Sheets and Scaffolds

The excellent protein protection effect of AqueSpheres (prepared by the present and our previous inventions [5,8]) is also useful for loading protein therapeutics to various polymer-based devices and systems in addition to microspheres. FIGS. 12A and 12B show the microscopic images of protein-containing AqueSpheres dispersed in a PLGA sheet and a PLGA scaffold. For preparation of these polymer devices, AqueSpheres were simply suspended in a PLGA solution (dissolved in an organic solvent), and shaped to designed form prior to solvent evaporation. Since preparation of polymer sheets and scaffolds do not need to use a water phase as in S-O-W microencapsulation, the processes are much more easier and less hazardous to delicate proteins.

Example 9

Loading AqueSpheres Into PLGA Coatings on Stent Surfaces

The same preparation approach in Example 5 can readily be used for coating proteins onto drug eluting stents. AqueSpheres can simply suspended in a PLGA solution, then sprayed (or dipped) to a stent. FIG. 13 shows photograph of a stent coated with a layer of PLGA in which myoglobin-containing AqueSpheres are dispersed. FIG. 14 shows the release profiles of myoglobin from the PLGA coating on stents, for which the protein release rate varies as a function of polysaccharide content (dextran/protein ratio for same protein loading; See FIG. 12B).

Example 10

Improvement of Sustained-Release Profile of Proteins from Thermal Sensitive Gels In addition to hydrophobic polymer devices, AqueSpheres may also be used to improve protein sustained-release profiles from aqueous thermal sensitive gels. For example, PLA-PEG-PLA block copolymers is reported for in vivo gellation due to its unique nature: melting at a temperature below 15° C. but gelling at body temperature [22]. However, when this thermal sensitive gel-system was used to protein sustained-release, severe burst occurred due to insufficient permeability barriers [21]. If proteins are pre-loaded in AqueSpheres (prepared using the present and our previous [5,8] invention) and then dispersed in the thermal sensitive gel, their release from the gel may be slowed down. Although the thermal sensitive gel possesses an aqueous interior, AqueSpheres will not dissolve but remain as a separated phase due to its aqueous-phase separation nature with PEG (the aqueous part of the gel) [5,8,11]. Proteins pre-loaded in AqueSphers partitioned favorably in the polysaccharide phase of hydrated AqueSpheres, so that their concentration gradient from the gel matrix to body fluid (regarded as the diffusion driving force) may substantially reduce. FIG. 15 shows the microscopic images of AqueSpheres dispersed in the PLGA-PEG-PLGA thermal sensitive gels. The hydrophilic AqueSpheres are well stand as a separated phase within the aqueous environment of the gel. FIG. 16 compares the release profiles of BSA from thermal sensitive gels (PLGA-PEG-PLGA) with and without AqueSpheres in which the protein was pre-loaded. In the case that BSA was loaded in AqueSpehres prior to adding to the gel, the initial burst was significantly reduced (FIG. 16).

Example 11

Microencapsulation of Sub-Unit Vaccines

The formulation process for sustained-release dosage forms of proteins demonstrated in the present invention may immediately be applied to long-lasting sub-unit vaccines. It has been reported that polymer-based sustained-release microspheres prolonged antibody titers of sub-unit vaccines and induce cellular vaccines [14,15]. The microencapsulation methods of the present invention ensure antigenic proteins with tertiary structures to be microencapsulated and released in nature states (See above examples).

Moreover, antigen-containing AqueSpheres can be prepared as 100~200 nm in diameter using the present invention (due to the low surface tension of aqueous-aqueous emulsion or of aqueous phase separation). These nanometer-sized AqueSpheres can further be microencapsulated in polymer microspheres few microns in diameter, a size small enough to be phagocytozed by some antigen presenting cells (APC). Therefore, antigenic proteins may be loaded in such "engulfable" microspheres and be released (in the nature state) inside of APC to stimulate T-Cell responses. FIG. 17 shows the electro-microscopic images for nanometer-sized AqueSpheres containing a model subunit vaccine (for hepatitis E) and PLGA microspheres containing such AqueSpheres.

Example 12

Preparation of Polymer Microspheres Using Solid-in-Oil-in-Oil-in-Water (S-O-O-W) Method Polysaccharide particles of diameter ranged from 0.5-5 microns were added to an ethyl acetate solution of PLGA, followed by stirring. The formed suspension was then added into glycerin with volume ratio of 1/5 to 1/15 under stirring. This operation led to an emulsion of which the polysaccharide particles were isolated in the dispersed phase. This emulsion was then added into cold water containing NaCl under slow stirring for 2-3 hours. During this time, the polymer dispersed phase was hardened to PLGA particles. The PLGA particles were then rinsed with water and subjected to a freeze-dryer for lyophilization. Ths PLGA microspheres containing polysaccharide particles in their matrix were harvested.

REFERENCES

[1] Sah, H.; Protein behavior at the water/methylene chloride interface; J. Pharm. Sci., 1999, 88, 1320-1325.
[2] Putney, S. D.; Burke, P. A.; Improving protein therapeutics with sustained-release formulations; Nature Biotechnol., 1998, 16, 153-157.
[3] Verrechia, T.; Huve, P.; Basile, D.; Veillard, M.; Spenlehauer, G.; Couvreur, P.; Adsoption/desorption of human serum albumin at the surface of poly(lactic acid) nanoparticles prepared by solvent evaporation process. J. Biomad. Mater. Res. 1993, 27, 1019-1028.
[4] Cleland, J. L., Jones J. S., Stable formulations of recombinant human growth hormone and interferon-gama for microencapsulation in biodegradable microspheres. Pharm. Res., 1996. 13(10): p. 1464-1475.
[5] Jin, T.; Chen, L.; Zhu, H.; Stable polymer aqueous-aqueous emulsion and its uses thereof, U.S. Pat. No. 6,805,879.
[6] Johnson, O. L., The stabilization and encapsulation of human growth hormone into biodegradable microspheres. Pharm. Res., 1997. 14(6): p. 730-737.
[7] Morita, T., Horikiri, Y., Yamahara, H., Suzuki, T., Yoshino, H., Formation and isolation of spherical fine protein microparticles through lyophilization of protein-poly(ethylene glycol) aqueous mixture. Pharm. Res., 2000. 17(11): p. 1367-1373.
[8] Jin, T.; Zhu, H.; Zhu, J.; AqueSpheres, their preparation and uses thereof, US Patent Published Application 20030059402.
[9] Wang, N.; Wu, X.; A novel approach to stabilization of protein drugs in poly(lactic-co-glycolic acid) using agarose hydrogel, Intern. J. Pharm., 1998, 166: 1-14.
[10] Gustafsson, A.; Wennerstrom, H.; Tjerneld, F.; The nature of phase separation in aqueous two-phase systems, Polymer, 27, 1768-1770.
[11] Zaslavsky, B. Y.; Aqueous two-phase partitioning: physical chemistry and biological applications, Marcel Dekker, 1995, New York.
[12] Heller, M. C.; Carpenter, J. F.; Randolph, T. W.; Manipulation of lyophilization-induced phase separation: implication for pharmaceutical proteins, Biotechnol. Prog., 1997, 13: 590-596.
[13] Randolph, T. W.; Phase separation of excipients during lyophilization: effects on protein stability, J. Pharm. Sci., 1997, 86: 1198-1203.
[14] Jiang. W. L., Gupta. R. K., Deshpande. M. C., Schwendeman S. P. Biodegradable poly(lactic-co-glycolic acid) microparticles for injectable delivery of vaccine antigens, Adv. Drug. Dev. Rev. 2005, 57: 391-410
[15] Waeckerle-Men. Y., Groetrup. M. PLGA microspheres for improved antigen delivery to dendritic cells as cellular vaccines, Adv. Drug. Dev. Rev. 2005, 57:475-482
[16] Whiteside. T. L. Immune suppression in cancer: Effects on immune cells, mechanisms and future therapeutic intervention, Seminars in Cancer Biology, 2006, 16, 3-15
[17] Jang. S. H., Wientjes. M. G., Lu. D., Au. J. L.-S. Drug Delivery and Transport to Solid Tumors. Pharm. Res., 2003, 20(9):1337-1350
[18] Molema. G., Kroesen. B. J., Helfrich. W., Meijer. D. K. F., de Leij. L. F. M. H., The use of bispecific antibodies in tumor cell and tumor vasculature directed immunotherapy, J. Control. Rel., 2000, 64:229-239
[19] Dyall. R., Vasovic. L. V., Clynes. R. A. Nikolic-Zugic. J. Cellular requirements for the monoclonal antibody-mediated eradication of an established solid tumor. Eur. J. Immunol. 1999, 29:30-37
[20] Kwonn. Y. M., Kim. S. W. Biodegradable Triblock Copolymer Microspheres Based On Thermosensitive Sol-Gel Transition, Pharm. Res., 2004, 21(2): 339-343
[21] Zentner. G. M., Rathi. R., Shih. C., McRea. J. C., Seo Min-Hyo, Oh. H., Rhee. B. G. Mestecky. J., Moldoveanu. Z., Morgan. M., Weitman. S., Biodegradable block copolymers for delivery of proteins and water-insoluble drugs, J. Control. Rel. 2001, 72:203-215
[22] Jeong. B., Bae. H. Y., Lee. D. S., Kim. S. W., Biodegradable block copolymers as injectable drug-delivery systems, Nature, 1997, 388(28):860-862

The invention claimed is:

1. A method of preparing polysaccharide glassy particles comprising bioactive biological agents without using surface active agents, the method comprising the steps of:
   a) preparing a single-phase aqueous solution consisting of a polysaccharide, a soluble polymer, a bioactive biological agent, and optionally either a sugar or glycerol to stabilize the biological agent during lyophilization;
   b) freezing the aqueous solution prepared in step a) gradually, wherein the polysaccharide undergoes freezing-induced phase separation out from the solution;
   c) lyophilizing the frozen solution in step b) to powders;
   d) suspending the powder prepared in step c) in an organic solvent which dissolves the soluble polymer but not the polysaccharide;
   e) removing the supernatant of the suspension in step d) and collecting the remaining polysaccharide glassy particles.

2. The method of claim 1, wherein the biological agents are selected from the group consisting of proteins, peptides, DNA, RNA, vaccines, antibodies, and viruses.

3. The method of claim 1, wherein the polysaccharide is selected from the group consisting of dextran, starch, cellulose, and derivatives of dextran or cellulose.

4. The method of claim 1, wherein the soluble polymer is selected from the group consisting of polyethylene glycol (PEG), polyethylene oxide (PEO), poly(N-vinylpyrrolidone) (PVP) and polyvinyl alcohol (PVA).

5. The method of claim 1, wherein the sugar is selected from trehalose, mannitol, sucrose, lactose, and maltose.

6. The method of claim 1, wherein the concentration of the sugar is 1 w/w % in the aqueous solution.

* * * * *